(12) United States Patent
Carson et al.

(10) Patent No.: US 7,087,063 B2
(45) Date of Patent: Aug. 8, 2006

(54) ABRASION DEVICE AND METHOD

(75) Inventors: Robert Carson, Rahway, NJ (US);
Susanne Teklits Iobst, Maywood, NJ
(US); Salvatore E. San Philip,
Belleville, NJ (US)

(73) Assignee: **Unilever Home & Personal Care
USA, division of Conopco, Inc.**,
Greenwich, CT (US)

( * ) Notice: Subject to any disclaimer, the term of this patent is extended or adjusted under 35 U.S.C. 154(b) by 694 days.

(21) Appl. No.: 10/370,379

(22) Filed: Feb. 19, 2003

(65) Prior Publication Data

US 2004/0162565 A1 Aug. 19, 2004

(51) Int. Cl.
*A61B 17/50* (2006.01)
(52) U.S. Cl. .................................................. 606/131
(58) Field of Classification Search ............... 606/131, 606/161, 172, 180; 600/562, 564, 567, 570; 433/1; 604/289; 279/51, 57
See application file for complete search history.

(56) References Cited

U.S. PATENT DOCUMENTS

| | | |
|---|---|---|
| 2,712,823 A | 7/1955 | Kurtin |
| 2,867,214 A | 1/1959 | Wilson |
| 3,468,079 A | 9/1969 | Kaufman |
| 4,274,419 A | 6/1981 | Tam et al. |
| 4,538,612 A | 9/1985 | Patrick, Jr. |
| 5,325,857 A | 7/1994 | Nabai et al. |
| 5,380,337 A | 1/1995 | Romaine |
| 5,394,886 A | 3/1995 | Nabai et al. |
| 5,570,700 A | 11/1996 | Vogeler |
| 5,707,383 A | 1/1998 | Bays et al. |
| 5,800,446 A | 9/1998 | Banuchi |
| 5,879,326 A | 3/1999 | Godshall et al. |
| 5,888,034 A | 3/1999 | Greenberg |
| 6,136,008 A | 10/2000 | Becker et al. |
| 6,241,739 B1 | 6/2001 | Waldron |
| 6,258,044 B1 | 7/2001 | Lonky et al. |
| 6,283,978 B1 | 9/2001 | Cheski et al. |
| 6,299,620 B1 | 10/2001 | Shadduck et al. |
| 6,387,103 B1 | 5/2002 | Shadduck |
| 6,423,078 B1 | 7/2002 | Bays et al. |
| 2001/0018061 A1 | 8/2001 | Rhoades |
| 2002/0045907 A1 | 4/2002 | Sherman et al. |
| 2002/0087167 A1 | 7/2002 | Winitsky |
| 2002/0087168 A1 | 7/2002 | Winitsky |
| 2002/0107527 A1 | 8/2002 | Burres |
| 2002/0123675 A1 | 9/2002 | Trautman et al. |
| 2002/0143345 A1 | 10/2002 | Koefer et al. |

FOREIGN PATENT DOCUMENTS

| | | |
|---|---|---|
| EP | 1 086 719 A1 | 3/2001 |
| EP | 1 219 254 | 3/2002 |
| GB | 100 446 | 10/1916 |
| GB | 2 278 282 | 11/1994 |
| WO | 02/32331 | 4/2002 |

*Primary Examiner*—Anhtuan T. Nguyen
*Assistant Examiner*—Tuan V. Nguyen
(74) *Attorney, Agent, or Firm*—Ellen Plotkin; Edward A. Squillante, Jr.

(57) ABSTRACT

Device and technique using same for abrading a small sample of epidermis for bio-analytical processing and method of using same. The device removes small samples of epidermal tissue with efficiency, minimal discomfort, and no excess tissue removal. The device and method may be provided as part of a home-use kit for individualized analysis.

8 Claims, 5 Drawing Sheets

ABRASION DEVICE AND METHOD

FIELD OF THE INVENTION

The present invention relates to an abrasion device and method. More particularly, the present invention relates to an abrasion device and method for painlessly and bloodlessly sampling skin for analysis.

BACKGROUND OF THE INVENTION

Demonstrating efficacy of technology on human subjects is an essential part of successful achievement of commercialization of such technology. Human trials aimed at identifying benefits of a technology, such as a skin benefit technology, often require three to six months duration to visualize measurable effect. For example, retinoids are a particularly potent anti-aging technology in skin care, however, even retinoids require this lengthy period to elicit a visual change. Shorter term, e.g. 1 week, human studies may be developed. These shorter term stuedes are especially useful for screening or ranking a number of potential actives. Short term human studies rely on the collection of skin tissue samples which are typically undertaken by physicians taking relatively invasive biopsies of the skin, either full thickness (dermis and epidermis) or shave biopsies. These invasive skin sampling methods generally provide more tissue than is actually required for many assays for biomarkers that may indicate long term clinical efficacy after short term treatment.

Currently used sampling techniques include the following: full thickness punch biopsies, "nick" (small shave) biopsies and blister biopsies. Full thickness punch biopsies entail use of a razor-edged circular punch and a scalpel to remove a piece of tissue that can extend further than the dermis. "Nick", or small shave, biopsies involve the use of a scalpel to remove a pinched up portion of the skin surface. The full thickness punch biopsy and the shave biopsy techniques present the subject with considerable discomfort, require anesthesia (requiring administration by a physician), and pose potential harm. Methods of this type, involving gross removal of skin tissue in a procedure that is essentially surgical include: U.S. Pat. No. 5,325,857, U.S. Pat. No. 5,394,886, U.S. Pat. No. 5,380,337 and U.S. Pat. No. 5,570,700. Blister biopsies require the use of a vacuum applied to the skin surface to produce a blister, which is removed by scalpel. Suction blister epidermal sampling provides the desired epidermal samples, however, this method requires a blistering period of about two hours, during which time changes can occur to the biochemistry of the epidermal skin cells, such as the degradation of RNA.

Dermabrasion tools and techniques used in treating pitted and disfigured skin involve what are essentially power tools and involve no harvesting and processing of sampled tissue material. U.S. Pat. No. 6,423,078 relates to surgical abrasion using diamond grit and U.S. Pat. No. 5,800,446 relates to an abrasive tip, however, both of these devices remove considerably more tissue than they are able to harvest.

There is a need for a sampling device and technique that does not require the presence of a physician, is minimally invasive, does not remove excess tissue, can be done with minimal discomfort and that provides a sample large enough for modern biochemical analysis.

SUMMARY OF THE INVENTION

To attenuate the shortcomings of prior devices and techniques, a novel abrasion device assembly and epidermal sampling technique have been developed.

In a first aspect, the present invention provides an abrasion device for sampling small amounts of epidermal cells from a skin surface of an individual. The assembly includes an actuator device comprising a central shaft conjoined with a handle device having a handle extending from it. The central shaft has a central opening therein. The assembly is further provided with a probe disposed centrally and releasably within the central opening of the actuator device. The probe comprises a cylindrical rod having a distal end and terminating in an abrasive surface at a cross-sectional proximal end thereof. The abrasive surface is appropriately textured and has a small cross-sectional diameter for abrasion and harvesting of epidermal cells. A cylindrical positioning sleeve is provided, comprising a cylindrical rod having a central opening therein of a larger diameter than the central shaft. The cylindrical rod has a proximal end and a distal end, a threaded surface extending from a selected position on said cylindrical rod and terminating at distal end. The positioning sleeve further includes a first locking ring adjustably positioned along the threaded surface and a second locking ring adjustably positioned from the distal end to adjacent the first locking ring. The positioning sleeve is releasably and adjustably positioned over the actuator device so that a desired length of the probe extends therefrom.

In a second aspect, the present invention provides a method for sampling small amounts of epidermal cells from a skin surface of an individual using the abrasion device in accordance with the first aspect. Upon being pressed against the skin surface with the abrasive surface, the probe abrades a small sample of epidermal tissue.

In another aspect, the present invention is a kit including the abrasion device in accordance with the first aspect. The kit is suitable for consumer use and does not require a physician's assistance.

In a further aspect, the present invention provides a method for assembling the abrasion device in accordance with the first aspect. Assembly includes the steps of: (a) securing the collet to the driver rod, (b) inserting the probe into the collet, (c) inserting the secured driver rod in the central opening of the central shaft of the actuator device, (d) tightening the knurled disc over the actuator device, thereby securing the driver rod therein and forcing the collet to grip the probe, and (e) sliding the positioning sleeve over the central shaft; thereby allowing a desired length of probe to protrude and extend beyond the proximal end of the positioning sleeve.

For a more complete understanding of the above and other features and advantages of the invention, reference should be made to the following description of the preferred embodiment.

BRIEF DESCRIPTION OF THE DRAWINGS

The invention will be better understood by way of the following detailed description of a preferred embodiment, with reference to the appended drawings in which.

DETAILED DESCRIPTION OF THE INVENTION

As used herein, the term "comprising" means including, made up of, composed of, consisting and/or consisting essentially of. Except in the operating and comparative examples, or where otherwise explicitly indicated, all numbers in this description indicating amounts or ratios of material or conditions of reaction, physical properties of materials and/or use are to be understood as modified by the word "about".

The term "harvesting" as used herein refers to the picking up of debris of abraded epidermal cells.

The term "skin" as used herein includes the skin on or in the face, mouth (epithelial cells), neck, chest, back, arms, hands, legs, and scalp.

The device and method of the present invention involve the removal of the upper skin layer with a manual, mechanically driven abrasive probe. Using the inventive device and method, the epidermis, including the basal layer of the epidermis, is removed, thereby effectively sampling the whole epidermis. Various quantities of epidermis may be obtained by varying the diameter of the probe. The small quantities of epidermis obtained using the inventive device and method have been found to have great utility in a variety of bio-analytical applications, such as determinations of RNA, protein, genomic DNA, minerals and other metabolites.

Figure 1:
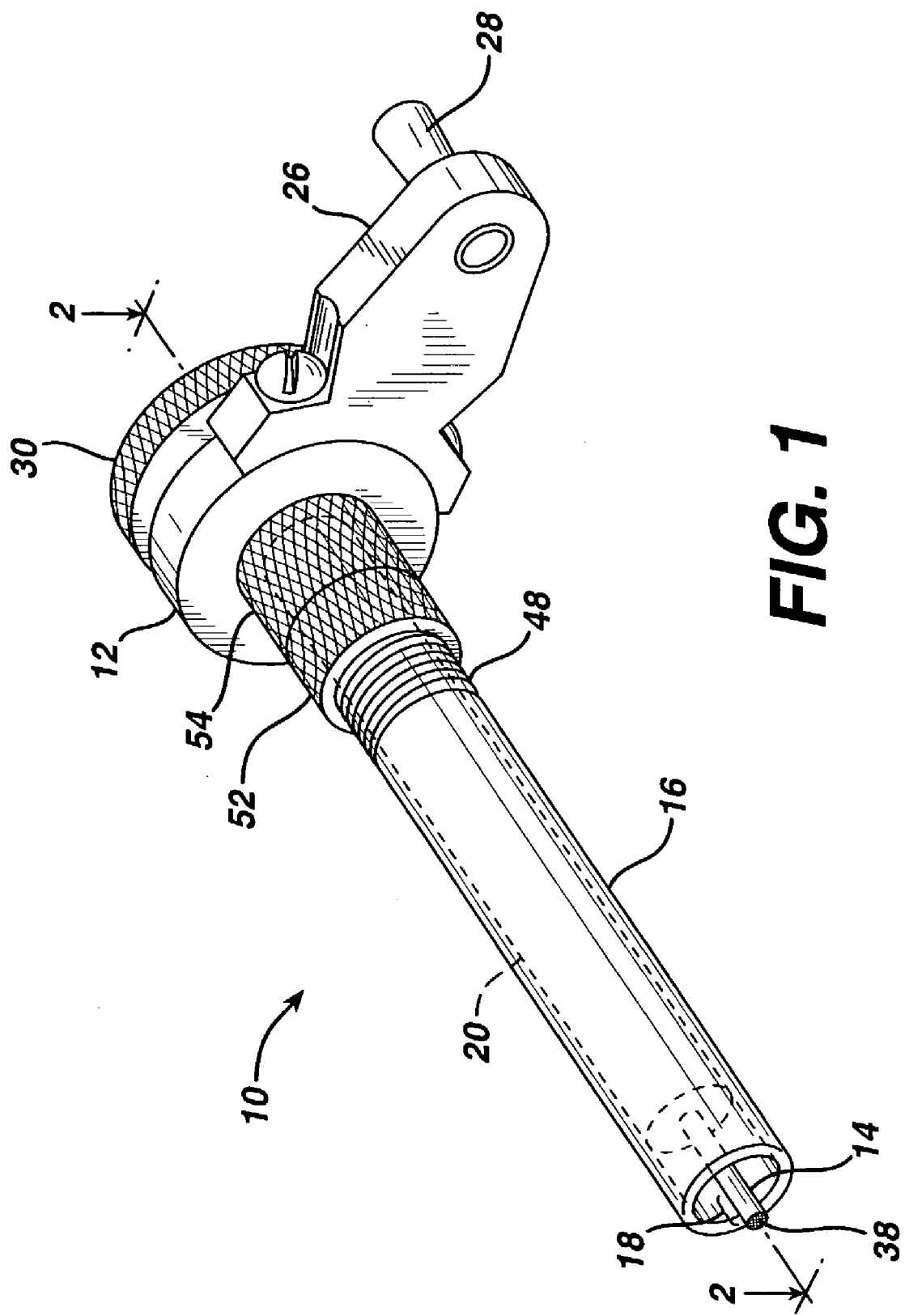
FIG. 1 is a perspective view of an assembled abrasion device according to one preferred embodiment.
Figure 1A:
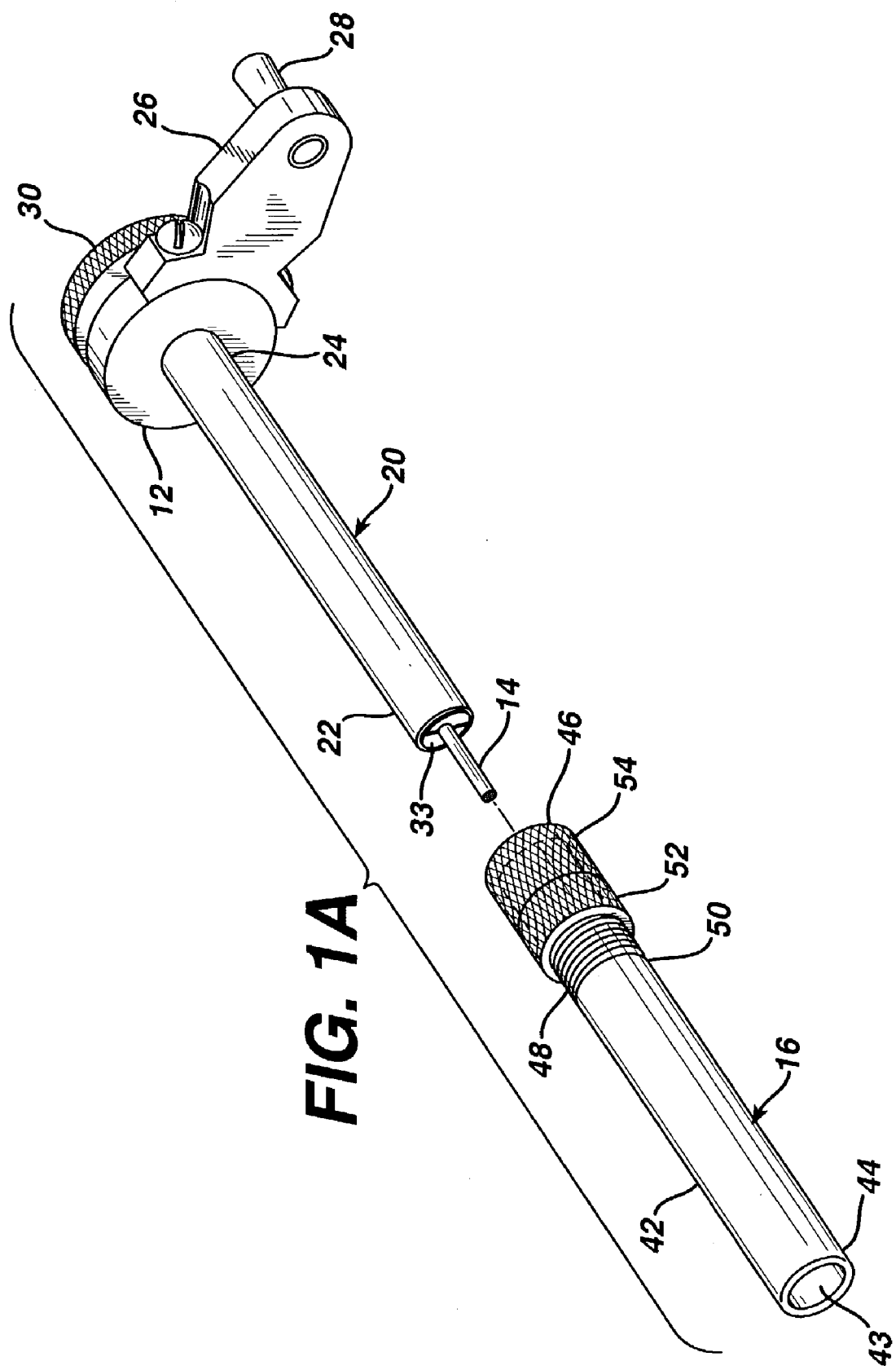
FIG. 1A is an exploded perspective view of the abrasion device of FIG. 1, with the sleeve removed.

With reference to FIGS. 1 and 1A, in one preferred embodiment, an abrasion device 10 for sampling small amounts of epidermal cells from a skin surface of an individual includes an actuator device 12, a probe 14 capable of being disposed centrally and releasably therein, and a cylindrical positioning sleeve 16 capable of being releasably and adjustably positioned over actuator device 12, so that a desired length 18 of probe 14 extends therefrom.

Figure 1B:
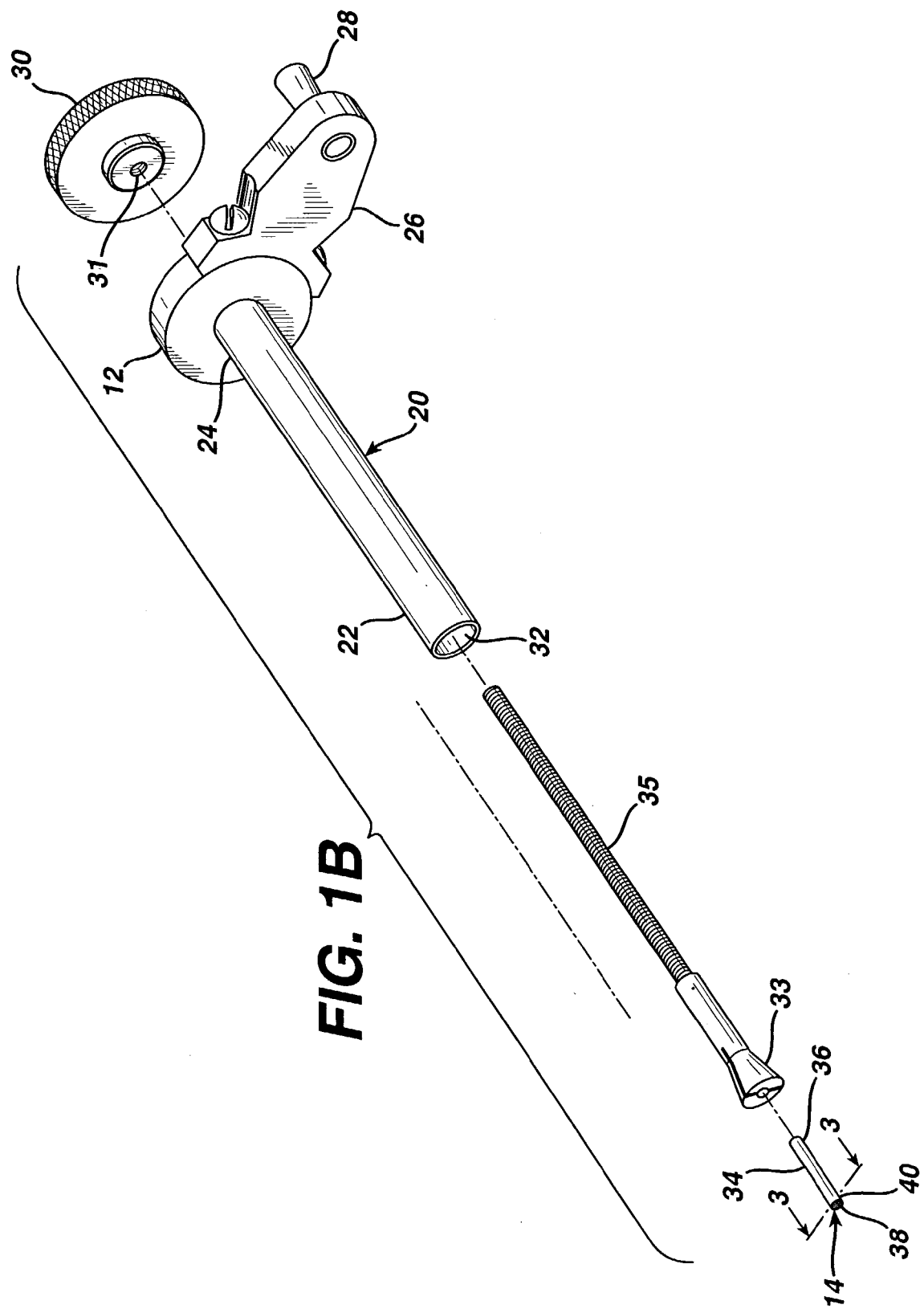
FIG. 1B is an exploded perspective view of the actuator device and probe of the abrasion device of FIG. 1.

With reference to FIG. 1B, actuator device 12 includes a cylindrical central shaft 20 having a proximal end 22 and a distal end 24 terminating in a handle device 26 which has a handle 28 protruding perpendicularly therefrom. Actuator device is further provided with a knurled disk 30 positioned co-axially with shaft 20 and secured substantially centrally onto handle device 26 as will be discussed hereinbelow with reference to FIG. 2. Knurled disk 30 has a threaded opening 31 centrally disposed therein.

Figure 2:
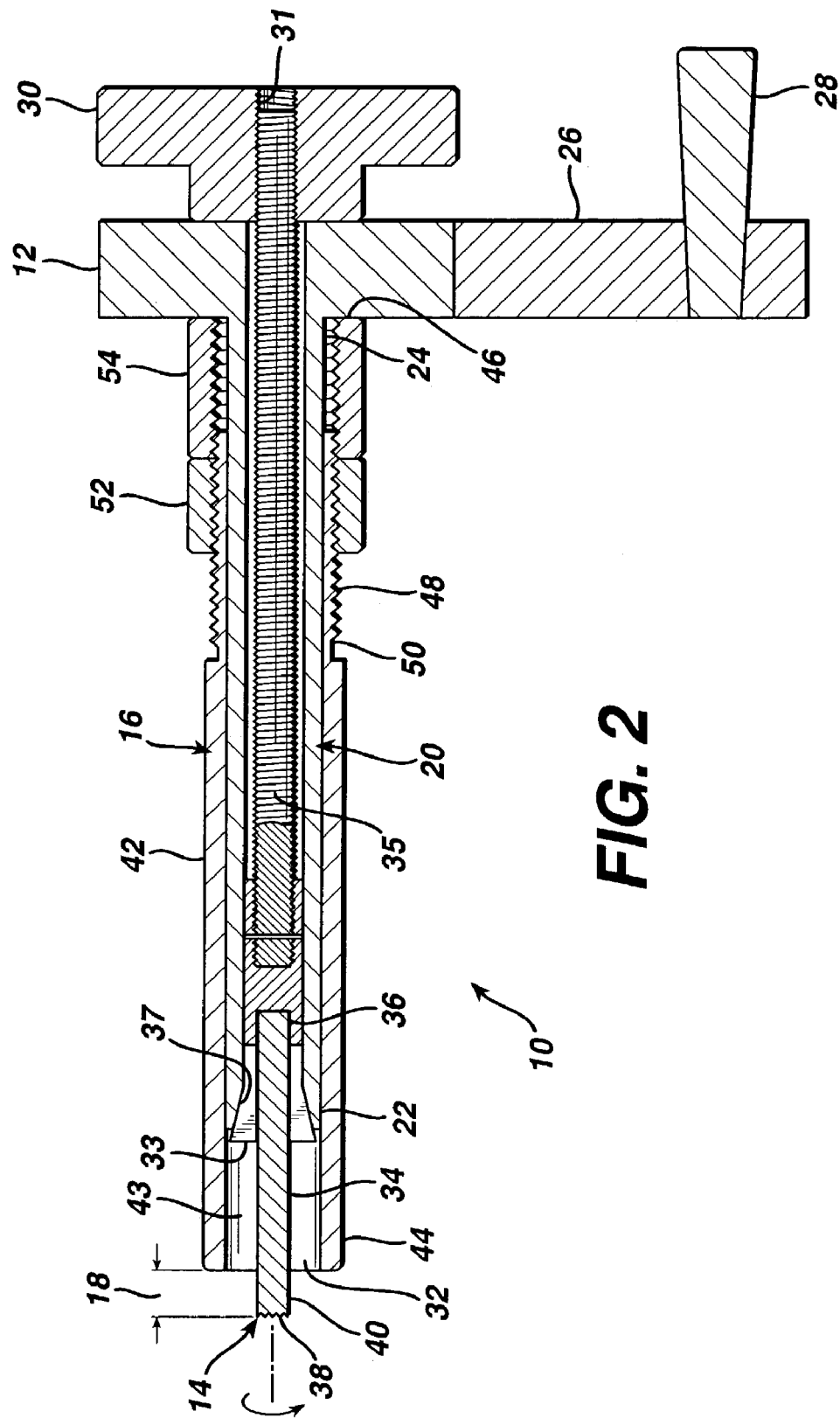
FIG. 2 is a cross-sectional view taken on the line 2—2 in FIG. 1.

With reference to FIG. 2, central shaft 20 has a central opening 32 situated therein, extending from proximal end 22 to distal end 24 thereof, starting with a larger diameter frusta-conical portion at proximal end 22 and forming a seat 37 as the frusta-conical portion tapers into a cylindrical portion and extends toward distal end 24. A collet 33 is releasably seated in seat 37 and releasably fixed to a threaded cylindrical driver rod 35 also disposed within central opening 32, which in turn is connected to knurled disk 30 by threaded screw cooperation at opening 31, thereby securing knurled disk 30 onto handle device 26. Collet 33 is split and compressible so that when it comes into seat 37, it is compressed to hold probe 14. With reference to FIGS. 1 and 1A, positioning sleeve 16 comprises a cylindrical rod 42 with a central opening therein 43 of a larger diameter than central shaft 20. Positioning sleeve 16 has a proximal end 44 and a distal end 46, having a threaded surface 48 extending from a selected position 50 on cylindrical rod 42 and terminating at distal end 46. Positioning sleeve 16 further includes a first locking ring 52 having a threaded cylindrical cavity therein to cooperate with and adjustably positioned along threaded surface 48, and a second locking ring 54 having a threaded cylindrical cavity therein to cooperate with threaded surface 48 and adjustably positioned along threaded surface 48 from distal end 46 to adjacent first locking ring 52.

With reference to FIG. 1B, probe 14 includes a cylindrical rod 34 having a distal end 36 and terminating in an abrasive surface 38 at a cross-sectional proximal end 40 thereof, which may be in the form of a disk, and appropriately textured for abrasion. Rod 34 may be of any small size suitable for sampling epidermal tissue and appropriately sized to cooperate with collet 33. Preferably, rod 34 is about 1 mm to about 10 mm in cross-sectional diameter. Cylindrical rod 34, and in turn abrasive surface 38, preferably has a diameter of about 1.5 mm.

Figure 3:
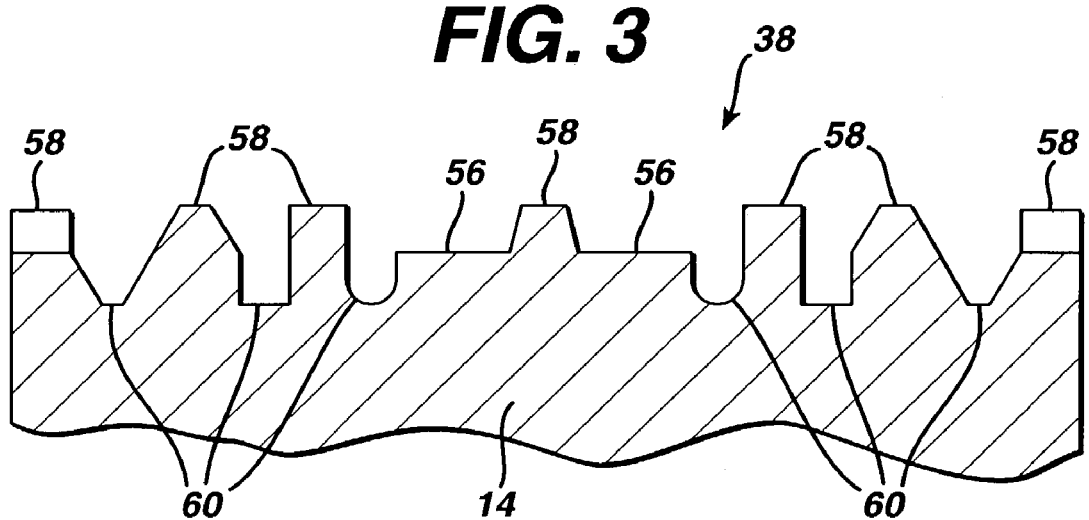
FIG. 3 is a cross-sectional view taken along line 3—3 in FIG. 1B.
Figure 4:
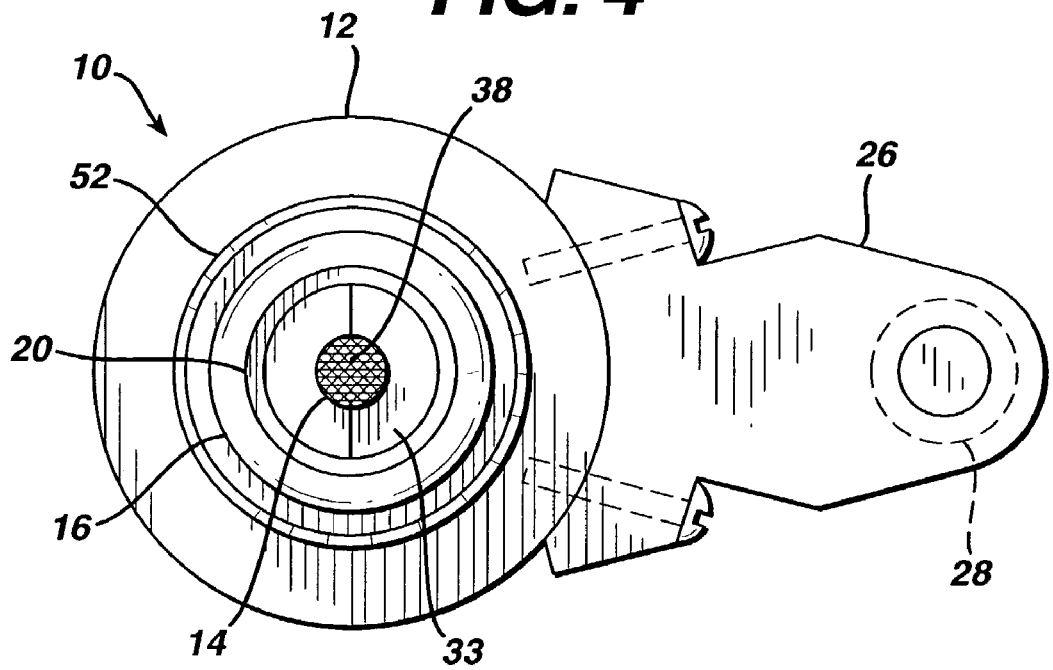
FIG. 4 is an enlarged top view of the abrasive surface of a probe in an abrasion device of FIG. 1.

With reference to FIG. 3, abrasive surface 38 of probe 14 includes a flat surface area 56 having a plurality of peaks 58 and troughs 60 extending upward and downward, respectively, relative thereto and positioned along flat surface area 56 in any configuration, including random or patterned configuration. Preferably, as shown in FIG. 4, the configuration of peaks 58 and troughs 60 will be patterned, or symmetrical, due to ease of manufacture.

Peaks 58 and troughs 60 may be of any three-dimensional shape, thereby having any cross-sectional shape. Preferably, for better abrasion, the cross-sectional shape of peaks 58 (or troughs 60 in the absence of peaks 58) includes an angle relative to the plane of flat surface area 56, such as that of a triangle, rectangle, hemisphere, trapezoid, or another geometry including an angle. More preferably, the cross-sectional geometrical shape includes a sharp angle that will form a sharp edge in the overall three-dimensional shape of peaks 58 or troughs 60.

Most preferably, the cross-sectional geometry of troughs 60 is a hemisphere for maximum capacity.

In one aspect of the invention, abrasive surface 38 may be comprised of only troughs 60. In another aspect, abrasive surface 38 may be comprised of only peaks 58.

The number and size of peaks 58 and troughs 60 is determined by the criteria that the Harvesting Volume be greater than or equal to the Abrasion Volume. Harvesting Volume as referred to herein is intended to mean the volume capacity of the sum of the volumes of troughs 60 plus the interstitial volume between peaks 58 (if any), while Abrasion Volume as referred to herein is intended to mean the volume of skin sample collected. This criteria ensures that substantially all the tissue abraded shall be harvested.

With reference to FIGS. 1A and 1B, to assemble abrasion device 10, collet 33 is secured to driver rod 35 and probe 14 inserted into collet 33. Driver rod 35, in turn, is inserted in central opening 32 of central shaft 20 of actuator device 12. Tightening knurled disc 30 over actuator device 12 secures driver rod 35 therein and forces collet 33 into seat 37, thereby gripping probe 14 within collet 33. Positioning sleeve 16 is slid over central shaft 20, allowing desired length 18 of probe 14 to protrude and extend beyond proximal end 44 of positioning sleeve 16 while second locking ring 54 is at distal end 24 of central shaft 20 of actuator device 12. Desired length 18 is determined by the degree of pressure desired to be applied against the skin in such a way as to substantially avoid penetration of the skin layers below the epidermis. Preferably, the depth of skin penetration is about 100 micro m.

In use, after sterilizing probe 14 and assembling abrasion device 10, positioning sleeve 16 is held such that second locking ring 54 is at distal end 24 of central shaft 20 of actuator device 12, adjacent handle 28 thereof. Handle 28 is rotated manually, causing central shaft 20 to rotate within positioning sleeve 16, thereby causing rotation of probe 14, wherein upon being pressed lightly against the skin surface with abrasive surface 38, probe 14 is capable of abrading a small sample of epidermal tissue by the rotating action against the skin. Second locking ring 54 may be adjusted along threaded surface 48, causing it to move closer or further from first locking ring 52, thereby adjusting the length of positioning sleeve 16. Adjusting the overall length of positioning sleeve 16 in turn adjusts the desired length 18 of protrusion of probe 14, thereby allowing for control of pressure applied to the skin and preventing excessive penetration of the skin. Flat surface area 56 of abrasive surface 38 of probe 14 also provides control of the depth of abrasion, as the probe will tend not to penetrate beyond the contact of skin with flat surface area 56. Rotation effectively removes epidermal tissue, which adheres to abrasive surface 38. Small amounts of epidermal tissue are removed, preferably about 0.00001 cu cm to about 0.001 cu cm, more preferably about 0.0003 cu cm (about 300 micro g). After the sample is taken, probe 14 is released from collet 33, and the epidermal sample collected on or in abrasive surface 38 may be submitted for analysis. Suitable analyses include determination of biochemical markers, RNA, protein, genomic DNA, minerals and other metabolites.

Abrasion device 10 allows quick, substantially bloodless epidermal sample excission (unlike biopsies), and leaves minimal or no residual scar (unlike surgical biopsies). Compared to the suction blistering technique, which takes about two hours and punch biopsy, which takes about two minutes, abrasion may be performed in about 0.001 to about 60 seconds, preferably about 10 to about 30 seconds. The speed of sampling offers the advantage of obtaining real time samples and limits sample degradation.

EXAMPLE 1

This example demonstrates the use of abrasion device 10 to provide efficient epidermal tissue collection with a substantial absence of scar, as compared to that by punch biopsy. Scar scores were obtained from grading 3 subjects in a clinical study in which both punch biopsies and epidermal abrasions were taken.

Abrasion device 10 was used in accordance with the method described hereinabove.

The punch biopsy procedure used in the study is as follows: A site on the forearm is anesthesized (via injection) with 1% Lidocaine with epinephrine and allowed to get numb. A 3 mm Accupunch (brand name) sterile, disposable biopsy punch is used to take the biopsy. The site on the skin is closed with one suture, then Bacitracin and a band-aid are applied. The suture is removed about 10 days later.

Test sites on three clinical study subjects who had punch biopsy and epidermal abrasion procedures conducted in a recent human clinical study were examined by clinicians to determine the level of scarring induced by both procedures. An index of 0–4 was used (see the Tables below).

TABLE 1

Scarring Index

| Score | Description |
|---|---|
| 0 | No scar |
| 1 | Faintly visible scar (not raised, slight discoloration compared to surrounding tissue, superficial) |
| 2 | Visible scar (not raised, discoloration presenting as hyper- or hypo-pigmentation, compared to surrounding tissue, still superficial) |
| 3 | Raised scar, deeper depth than above, discoloration presenting as hyper- or hypo-pigmentation or erythema |
| 4 | Raised scar, severe pigmentation changes compared to surrounding tissue, keloid formation |

TABLE 2

Punch Biopsy "Scar Score"

| ID | Biopsy 1 taken on Day 1 | Biopsy 2 taken on Day 2 | Biopsy 3 taken on Day 55 | Comments |
|---|---|---|---|---|
| 1 | 1.5 | 1.5 | 1.5 | Graded on Day 111 |
| 2 | 2.5 | 2.5 | 2.5 | Graded on Day 111 |
| 4 | 3.0 | 3.0 | 3.0 | Graded on Day 111 |

TABLE 3

Epidermal Abrasion "Scar Score"

| ID | Abrasion series 1 taken on Day 1 | Abrasion series 2 taken on Day 2 | Abrasion series 3 taken on Day 28 | Abrasion series 4 taken on Day 55 | Comments |
|---|---|---|---|---|---|
| 1 | 0 | 0 | 0 | 0 | Score applies to all 12 sites, 6 on arm and 6 on forehead. Graded on Day 111 |
| 2 | 0 | 0 | 0 | 0 | Score applies to all 12 sites, 6 on arm and 6 on forehead. Graded on Day 111 |
| 4 | 0 | 0 | 0 | 0 | Score applies to all 12 sites, 6 on arm and 6 on forehead. Graded on Day 111 |

All of the 9 punch biopsy sites had visible scars from the punch biopsy procedure. None of the epidermal abrasion sites (144 sites in total—6 abrasions×4 time points×2 sites=48 sites per subject×3 subjects=144 sites) exhibited any scarring from the epidermal abrasion procedure.

The inventive device and method advantageously provide efficiency, minimal discomfort, avoidance of excess tissue removal and scarring, and the capability to efficiently harvest and collect epidermal samples for analysis. The small amount of epidermis sampled results in minimal discomfort to the subject and a substantial absence of scar. The device therefore lends itself to multiple sampling from one individual. Therefore, the device and method are useful in investigations of individual variation in skin biology and product efficacy, such as for example providing crucial tissue sampling to enable genomic analysis of skin to be assessed before and after product application. The device and method may also be useful in skin diagnostic activities.

This technique could be widely employed in clinical testing as it is minimally invasive and much more acceptable to subjects than current sampling methods. It also may be capable of adaptation for home-use skin sampling/analysis kits, which may include abrasion device assembly 10 together with instructions for use and analysis and an analytical device.

While the present invention has been described herein with some specificity, and with reference to certain preferred embodiments thereof, those of ordinary skill in the art will recognize numerous variations, modifications and substitutions of that which has been described which can be made, and which are within the scope and spirit of the invention. It is intended that all of these modifications and variations be within the scope of the present invention as described and claimed herein, and that the inventions be limited only by the scope of the claims which follow, and that such claims be interpreted as broadly as is reasonable. Throughout this application, various publications have been cited. The entireties of each of these publications are hereby incorporated by reference herein.

We claim:

1. An abrasion device for sampling small amounts of epidermal cells from a skin surface of an individual, comprising:
    an actuator device comprising a central shaft having a proximal end and a distal end conjoined with a handle device having a handle extending therefrom; said central shaft having a central opening therein extending from said proximal end to said distal end;
    a probe capable of being disposed centrally and releasably within said central opening of said actuator device; said probe comprising a cylindrical rod having a distal end and terminating in an abrasive surface at a cross-sectional proximal end thereof; said abrasive surface being appropriately textured and having a small cross-sectional diameter for abrasion and harvesting of said epidermal cells;
    a cylindrical positioning sleeve comprising a cylindrical rod having a central opening therein of a larger diameter than said central shaft; said cylindrical rod having a proximal end and a distal end, a threaded surface extending from a selected position on said cylindrical rod and terminating at distal end, said positioning sleeve further comprising a first locking ring adjustably positioned along threaded surface and a second locking ring adjustably positioned from said distal end to adjacent said first locking ring;
    a knurled disc positioned co-axially with said shaft, said knurled disc having a threaded opening centrally disposed therein; and
    a threaded cylindrical driver rod in screw cooperation with said knurled disc;
wherein said positioning sleeve is releasably and adjustably positioned over said actuator device so that a desired length of said probe extends therefrom.

2. The abrasion device of claim 1, further comprising a collet seated within said central opening and releasably fixed to said cylindrical driver rod.

3. The abrasion device of claim 1, wherein said abrasive surface of said probe includes a flat surface area having a plurality of peaks and troughs extending therefrom.

4. The abrasion device of claim 3, wherein said peaks have a cross-sectional geometric shape that includes an angle selected from the group consisting of a triangle, rectangle, hemisphere, trapezoid, or a combination thereof.

5. The abrasion device of claim 3, wherein said troughs have a cross-sectional geometry of a hemisphere.

6. The abrasion device of claim 3, wherein the number and size of peaks and troughs is determined by the criteria that the Harvesting Volume be greater than or equal to the Abrasion Volume.

7. A kit including the abrasion device of claim 1.

8. The kit of claim 7, wherein use of said kit by a consumer does not require the assistance of a physician.

* * * * *

UNITED STATES PATENT AND TRADEMARK OFFICE
CERTIFICATE OF CORRECTION

PATENT NO. : 7,087,063 B2  Page 1 of 1
APPLICATION NO. : 10/370379
DATED : August 8, 2006
INVENTOR(S) : Robert Carson et al.

It is certified that error appears in the above-identified patent and that said Letters Patent is hereby corrected as shown below:

On Title Page, col. 1 Item (75)

Please correct the "Inventors" section to read as follows:

Robert Carson, Rahway, NJ (US); Susanne Teklits Iobst, Maywood, NJ (US); Salvatore E. San Philip, Belleville, NJ (US); Christina H. Arce, Cliffside Park, NJ (US); Carol Feinberg, Wayne, NJ (US)

Signed and Sealed this

Nineteenth Day of December, 2006

JON W. DUDAS
*Director of the United States Patent and Trademark Office*